(12) United States Patent
Ebesu et al.

(10) Patent No.: US 12,594,360 B1
(45) Date of Patent: *Apr. 7, 2026

(54) HEMOSTATIC MICROPARTICLES AND DRESSING

(71) Applicant: Oceanit Laboratories, Inc., Honolulu, HI (US)

(72) Inventors: Joanne S. M. Ebesu, Waipahu, HI (US); Jacob Pollock, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/879,676

(22) Filed: Aug. 2, 2022

Related U.S. Application Data

(62) Division of application No. 15/296,001, filed on Oct. 17, 2016, now Pat. No. 12,427,224.

(60) Provisional application No. 62/242,292, filed on Oct. 15, 2015.

(51) Int. Cl.
  *A61L 26/00* (2006.01)
(52) U.S. Cl.
  CPC ....... *A61L 26/0038* (2013.01); *A61L 26/0023* (2013.01); *A61L 26/0066* (2013.01); *A61L 2300/60* (2013.01)
(58) Field of Classification Search
  None
  See application file for complete search history.

(56) References Cited

U.S. PATENT DOCUMENTS

| | | | |
|---|---|---|---|
| 6,465,626 | B1 | 10/2002 | Watts |
| 2006/0246121 | A1 | 11/2006 | Ma |
| 2011/0125089 | A1 | 5/2011 | Senderoff |

OTHER PUBLICATIONS

Yao et al. "pH sensitive chitosan/gelatin hybrid polymer network microspheres for delivery of cimetidine", Polymer International 39, 333-336 (Year: 1996).*
Liu et al. (Effects of the controlled-released basic fibroblast growth factor from chitosan-gelatin microspheres on human fibroblasts cultured on a chitosan-gelatin scaffold, Biomacromolecules8, 1446-1455 (Year: 2007).*
"Glutaraldehyde : Nature of the reagent" J. Mol. Bio. 65, 525-529 (Year: 1972).*

(Continued)

*Primary Examiner* — Isis A Ghali
(74) *Attorney, Agent, or Firm* — Fresh IP PLC; Clifford D. Hyra; Aubrey Y. Chen

(57) ABSTRACT

Disclosed herein is a method of manufacturing hemostatic particles, which involves heating and mixing a chitosan solution and a gelatin solution to form a chitosan/gelatin solution, adding the chitosan/gelatin mixture to oil containing an emulsifier/surfactant to form a combination of chitosan/gelatin and oil, heating and mixing the combination and then cooling and stirring the combination to form gelatin-chitosan microspheres (GCM), adding an aqueous solution of glutaraldehyde to the combination and stirring to cross-link the GCM, washing the GCM with emulsifier/surfactant to remove the oil, washing the GCM with a solvent to further remove excess oil, washing the GCM with alcohol to remove excess water, and drying the GCM.

3 Claims, 6 Drawing Sheets

200

(56) References Cited

OTHER PUBLICATIONS

Hussain et al. "Determination of Degree of Deacetylation of Chitosan and Their effect on the Release Behavior of Essential Oil from Chitosan and Chitosan-Gelatin Complex Microcapsules", International Journal of Advanced Engineering Applications, vol. 2, Iss. 4, pp. 4-12 (Year: 2013).

Peng et al. "Influence of chemical cross-linking on properties of gelatin/chitosan microspheres", Polymer-Plastic Technology and Engineering; vol. 51, Issue 4, 2012.

Chiono et al. "Genipin-crosslinked chitosan/gelatin blend for biomedical applications"; J. Matter Sci.; Matter Med.; 19: 889-898, 2008.

Malette et al. "Chitosan a new hemostatic", The Annals of Thoracic Surgery, vol. 36; Issue 1, July, 55-58 (Year: 1983).

Takahashi et al. "Study on hydrophilic properties of gelatin as a clinical wound dressing. II, Water-absorbing property and hemostatic effect of gelatin", The Tokushima Journal of Experimental Medicine, Dec. 1, 1993, 40(3-4); 169-175.

Nguyen "Crosslinked microspheres as drug delivery system for liver cancer", The University of New South Wales, Nov. 2008.

Zhu et al. "Chitosan/gelatin microspheres prepared by modified emulsification and ionotropic gelation", Microencapsulation, vol. 18, No. 2, 237-245 (Year: 2001).

Lui et al. "Enhanced hemostatic performance of tranexamic acid-loaded chitosan/alginate microparticles", Journal of Biomedicine and Biotechnology, vol. 2012, pp. 1-9 (Year: 2012).

Non-Final Office Action dated Feb. 21, 2019, issued in U.S. Appl. No. 15/296,001; 29 pages.

Final Office Action dated Aug. 1, 2019, issued in U.S. Appl. No. 15/296,001; 30 pages.

Non-Final Office Action dated Dec. 31, 2019, issued in U.S. Appl. No. 15/296,001; 25 pages.

Final Office Action dated Jul. 24, 2020, issued in U.S. Appl. No. 15/296,001; 26 pages.

Non-Final Office Action dated Jun. 9, 2021, issued in U.S. Appl. No. 15/296,001; 34 pages.

Final Office Action dated Nov. 15, 2021, issued in U.S. Appl. No. 15/296,001; 32 pages.

Non-Final Office Action dated Feb. 22, 2022, issued in U.S. Appl. No. 15/296,001; 42 pages.

* cited by examiner

100

200

800          802          804

900

908          910          912

902          904          906

Gauze          CG          DERT

Blood loss (% of initial body mass)

HEMOSTATIC MICROPARTICLES AND DRESSING

CROSS-REFERENCE TO RELATED APPLICATIONS

This application is a divisional of U.S. patent application Ser. No. 15/296,001, filed Oct. 17, 2016, which claims priority to U.S. Provisional Application No. 62/242,292, filed Oct. 15, 2015, each of which is hereby incorporated by reference in its entirety.

STATEMENT REGARDING FEDERALLY SPONSORED RESEARCH OR DEVELOPMENT

The invention described herein was made with U.S. government ("Government") support under Award W81XWH-11-1-0784, awarded by the United States Army Medical Research and Materiel Command (USAMRMC). As a result, the Government has certain rights in this invention.

FIELD

The application relates generally to hemostatic wound treatments.

BACKGROUND

Hemorrhage is the leading cause of preventable death in military trauma and the major cause of death in civilian trauma. Since approximately 90% of combat casualties occur prior to accessing a medical treatment facility, point of wound care is vital. More effective, instantaneous hemostasis wound treatments are urgently needed to prevent casualties due to uncontrolled blood loss.

Existing dressings designed to clot blood in traumatic wounds take more than several minutes to work, are not more efficient than plain gauze, are not conformable to wounds, are not easily removable from wound tissue, contain non-organic particles that can spread systemically, and some can cause additional tissue damage due to exothermic reactions with blood. WoundSeal, a blood-clotting powder, is a potassium ferrate-based product for topical use, not designed for internal injuries. Alginate dressings cause hemostasis by absorbing fluids and providing calcium ions necessary for normal blood clotting, but are not as effective for high-pressure and/or heavily bleeding wounds. Calcium alginates tend to swell, while sodium alginates tend to dissolve or gel in a wound bed.

Chitosan dressings work by adhering to tissue and sealing wounds, and also possess antimicrobial properties. In coagulation, chitosan (positively charged) interacts with the cell membrane of erythrocytes (negatively charged) leading to involvement of platelets and rapid thrombus formation. Chitosan is biocompatible and biodegradable. It is broken down by lysozyme in the body to glucosamine.

Other dressings containing fibrin, fibrinogen, thrombin and collagen are also used to control hemorrhage, but all of these products take from 3 to 5 minutes to clot blood in traumatic wound models. These products are involved in the coagulation cascade. In the presence of thrombin, fibrinogen is converted to fibrin. Thrombin also activates factor XIII, which stabilizes blood clots by promoting cross-linking of fibrin. This process requires calcium ions.

The primary component in gelatin, collagen, binds to circulating platelets with collagen-specific glycoprotein Ia/IIa surface receptors. The nearby endothelium and platelets release von Willebrand factor (vWF), which forms additional links between the platelets' glycoprotein Ib/IX/V and the collagen. The platelets localize to the extracellular matrix (ECM), which promotes collagen interaction with platelet glycoprotein VI. Binding of collagen to glycoprotein VI triggers a cascade resulting in activation of platelet integrins that mediate tight binding of platelets to the ECM and adhere platelets to the site of injury. Platelet activation is crucial to the initiation phase of blood coagulation.

An older related method and product used for the purpose of hemostasis is chitosan/alginate composite microparticles loaded with tranexamic acid.

Needs exist for improved hemostatic wound treatments and dressings.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

Embodiments of the present invention improve upon the prior art by taking advantage of the blood clotting effects of its components, which include chitosan, gelatin and/or collagen, and high surface area-to-volume ratio to immediately clot blood, and by in some embodiments including additional factors that enhance blood clotting.

Embodiments of the present invention have additional value since they can be made in several different form factors, such as a loose powder, a sprayable powder, a condensed powder, embedded into a gauze-type material, or enclosed in a porous pouch for ease of application to and removal from traumatic wounds. It may also be suspended in an aqueous or gelatinous vehicle for delivery to a wound site. In addition, the incorporation of additional chemical hemostatic compounds may further improve its hemostatic ability.

Embodiments of the present invention utilize a very pure form of chitosan, such as purified, medical grade chitosan, and are created in a novel process that has been discovered to result in a superior product for purposes of wound treatment/clotting. Prior art compositions of a related nature have not been recognized to be useful in such applications.

A new method involves heating and mixing a chitosan solution and a solution of gelatin or biocompatible polymer to form a chitosan/gelatin solution, adding the chitosan/gelatin mixture to oil containing an emulsifier/surfactant to form a combination of chitosan/gelatin and oil, mixing the combination and then cooling and stirring the combination to form gelatin-chitosan microspheres (GCM), adding an aqueous solution of a cross-linking agent to the combination and stirring to cross-link the GCM, washing the GCM, and drying the GCM.

The chitosan solution may be 1-10 weight % in 1-4% acetic acid and the gelatin solution may be 1-40 weight % in $dH_2O$. Heating of the chitosan and gelatin solutions may involve heating to 40-80° C., the chitosan/gelatin mixture may be added to the oil dropwise and the oil may be 20-40× volume oil, the emulsifier/surfactant may be polysorbate 80, the mixing of the combination may be performed at 35-40° C. and stirring and the cooling of the combination may include cooling to 10-20° C., the aqueous solution of the cross-linking agent may be a 10-75% aqueous solution of glutaraldehyde and the stirring of the aqueous solution of glutaraldehyde and combination may be performed for 1-3 hours, washing the GCM may involve washing the GCM with emulsifier/surfactant 3-6 times, washing the GCM with acetone 3-6 times, and washing the GCM with isopropyl alcohol 3-6 times, and drying the GCM may involve lyophilizing the GCM or air drying it at 4° C.

The chitosan solution may include ultrapure chitosan, with molecular weight range from 140-220 kilodaltons and degree of acetylation of 70-90%. The chitosan solution may include chitosan having molecular weight ranging from 4-140 kDa and degree of acetylation from 40-98%.

A composition formed by this method may contain GCM having a ratio of gelatin to chitosan by weight of approximately 1:0.3 and approximate microsphere diameters of 5-50 microns. The GCM may have a ratio of gelatin to chitosan by weight of approximately 1:0.2-1.1 and approximate microsphere diameters of 50-999 microns or 100-999 nanometers.

The solution of gelatin or biocompatible polymer may include Type B gelatin.

The solution of gelatin or biocompatible polymer may include at least one biocompatible polymer from the group consisting of: an alginate, a hyaluronate, carboxy methyl cellulose, carboxy methyl agarose, carboxy methyl chitosan, carboxy methyl dextran, and xanthan gum.

The method may also include one or more of a) adding one or more hemostatic agents to the mixture of chitosan and gelatin solutions prior to emulsification, and b) adsorbing one or more hemostatic agents onto the surface of the GCM after drying. The one or more hemostatic agents may include tranexamic acid. The one or more hemostatic agents may include tranexamic acid (TXA), adenosine diphosphate (ADP), fibrin, fibrinogen, thrombin, and/or calcium. The one or more hemostatic agents may include TXA and ADP, wherein the TXA is added in solution at 10 μL of 15 mg TXA/10 mL dH$_2$O and the ADP is added in solution at 1 microliter (μL) of 0.05 mM ADP.

The method may also include incorporating one or more bioactive agents into the GCM, selected from the group consisting of: antimicrobial agents, antibiotics, hormones, proteins, iodine, analgesics, and colloidal silver.

The cross-linking agent may include one or more from a group consisting of: genipin, glyoxal, dextran sulfate, 1,1,3,3-tetramethoxypropane, oxidized cyclodextrins, ethylene glycoldiglyceryl ether, ethylene glycol diglycidyl ether, diiosocyanate, and tripolyphosphate (TPP).

The method may further include centrifugation after cross-linking the GCM to separate particles, stirring the combination to form GCM may be performed at 10,000-20,000 rpm and stirring to cross-link the GCM may be performed at 5,000-10,000 rpm, whereby GCM nanoparticles are produced.

The emulsifier/surfactant may have a low hydrophilic-lipophilic balance value.

The cooling may decrease temperature of the combination to below 5° C.

The chitosan solution may include ultrapure chitosan with a molecular weight range from 4 to below 200 kilodaltons, for example from 4 to 190 kilodaltons.

A new treatment method includes recognizing a hemorrhaging wound in a patient and applying a composition formed by one of the above-described methods to the wound. Said wound may include an external laceration, an abrasion, a burn, an internal laceration, superficial cuts and scrapes, an arterial bleed, a venous bleed, dental or oral bleeds and incisions, and/or surgical incisions.

A new composition includes GCM having a ratio of gelatin to chitosan by weight of approximately 1:0.2-1.1 and approximate microsphere diameters of 50-999 microns or 100-999 nanometers.

These and further and other objects and features of the invention are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

DETAILED DESCRIPTION

Figure 1:
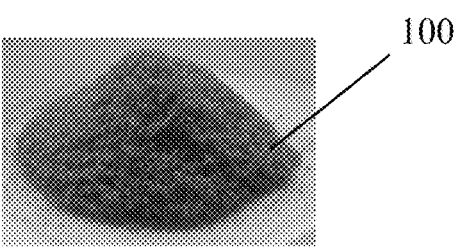
FIG. 1 is an image of lyophilized GCM (gelatin chitosan microspheres, also referred to "DERT").

Hemostatic microparticles and dressings will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The figures are not to scale. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

New polymeric microparticles include cross-linked chitosan and gelatin and are useful for medical purposes as hemostatic products that can be used to treat wounded tissue.

FIG. 1 is an image of lyophilized GCM (gelatin chitosan microspheres, also referred to "DERT") 100 created according to an embodiment of the present invention.

Figure 2:
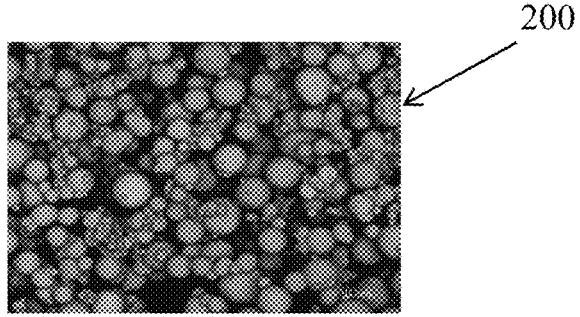
FIG. 2 is a microscopic image of lyophilized GCM at 40× magnification.

FIG. 2 is a microscopic image of lyophilized GCM 200 at 40× magnification.

Figure 3:
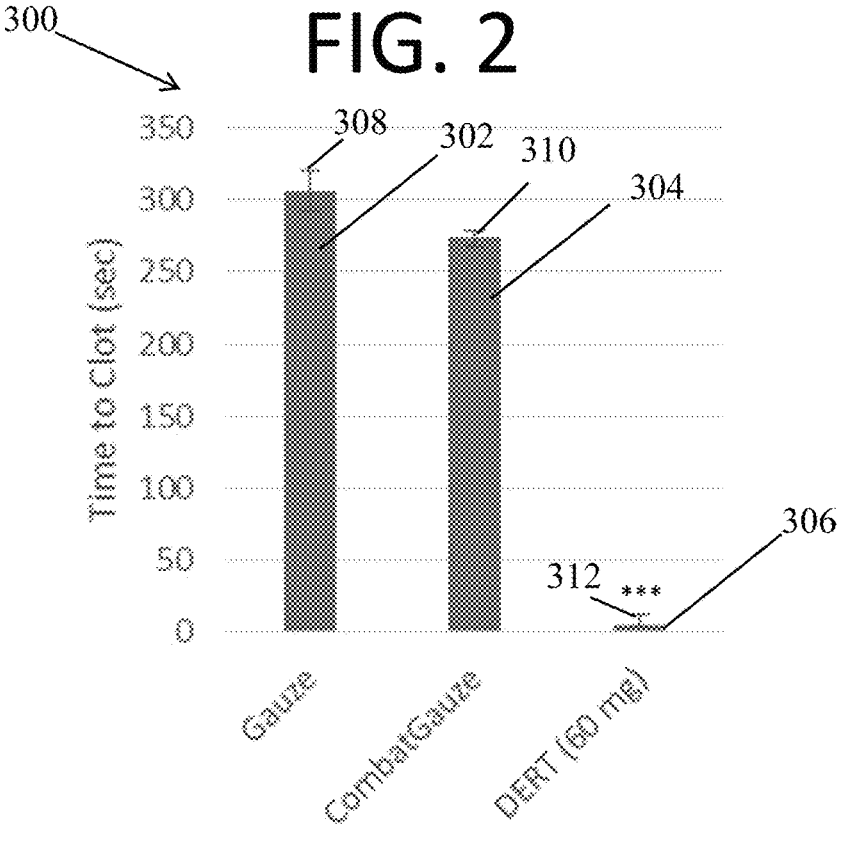
FIG. 3 is a chart showing hemostasis test results of GCM versus gauze and CombatGauze in sheep plasma, in an embodiment. ***, p<0.001.

FIG. 3 is a chart 300 showing hemostasis test results of clotting time for GCM 306 versus gauze 302 and Combat-Gauze 304 in sheep plasma, in an embodiment, with error bars 306, 302, 304, respectively. The results for DERT differ significantly from those of gauze and CombatGauze with p<0.001.

Figure 5:
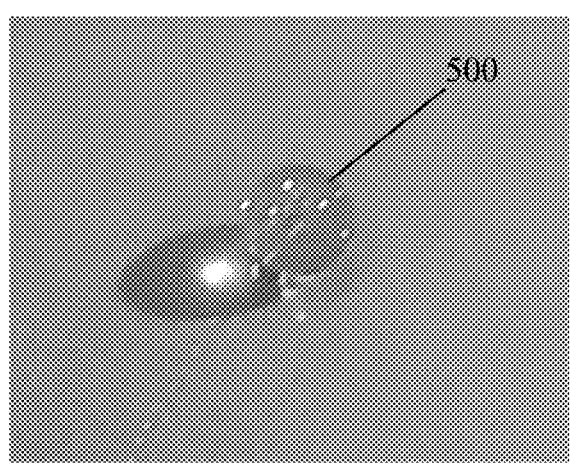
FIG. 5 is an image of a single GCM after glutaraldehyde fixation, approximate diameter 1 mm.

FIG. 5 is an image of a single GCM 500 after glutaraldehyde fixation, approximate diameter 1 mm.

Novel biopolymer microspheres have a high surface area plus intrinsic hemostatic ability that immediately clot blood in traumatic wounds to stop critical blood loss. Preliminary testing of the biopolymer microspheres (DERT or GCM) (See FIGS. 1 and 2) demonstrate that it can instantaneously clot sheep blood and plasma in vitro at relatively low concentrations (<0.10 g DERT/1.0 mL sheep blood or plasma), while comparable amounts (1.0 cm²) of gauze and QuikClot CombatGauze take about 4-5 minutes to clot blood in the same assay (FIG. 3). This instantaneous clotting is partially a result of absorption of the blood/plasma by the DERT, which will occur to some extent when it is utilized in a dried or lyophilized form, including in real-life applications. The inherent clotting abilities of both chitosan and gelatin are complemented by DERT's absorptive effect, since it serves to concentrate the blood's clotting factors and cells at the injury site. A combination of absorption with clotting is desirable in a hemostatic dressing.

Ex vivo testing of DERT versus other hemostatic wound treatments (<0.50 gm each) in artificially-perfused porcine livers (FIGS. 4A,4B) have demonstrated that it can clot simulated wounds in about 1 minute without applied pressure, over 2-5 times as fast as CombatGauze, WoundSeal, and gauze (see Table 1 in Example below).

DERT is biocompatible, biodegradable, bacteriostatic, fungistatic, and formulated with FDA-approved materials. Its bacteriostatic and fungistatic properties are imparted by chitosan.

DERT technology is transformative because it is a novel form factor as well as a biodegradable, biocompatible formulation that is not exothermic. It is easily conformable, and is based on the hemostatic abilities of chitosan and collagen. DERT may be used to minimize blood loss in battlefield injuries, thus reducing the casualty rate due to uncontrolled hemorrhage. In the civilian world, DERT may be used by first responders as well as lay persons to minimize hemostatic trauma.

In embodiments of the present invention the ratio of gelatin to chitosan by weight ranges from 1:0.2 to 1:1, but preferably 1:0.3 Ultrapure (medical grade) chitosan is used, preferably in the molecular weight range from 140-220 kilodaltons, although chitosan with lower molecular weights (4-140 kDa) or higher molecular weights (220-2000 kDa) may be used with less hemostatic efficacy. Related prior art compositions have used higher molecular weight chitosan, from 200-460 kDa.

The term "chitosan" will be understood by those skilled in the art to include all derivatives of chitosan, or deacetylated chitin, or poly-N-acetyl-D-glucosamine, in which most of the N-acetyl groups have been removed by hydrolysis. The chitosan in embodiments has a positive charge.

The chitosan is in embodiments water soluble with a degree of deacetylation between 40% and 98%, and in some such embodiments between 70 and 90%.

The gelatin used in embodiments of the present invention is preferably type B, which is anionic and processed using an alkali treatment. Gelatin can absorb between 5 to 10 times its weight in water.

Figure 10:
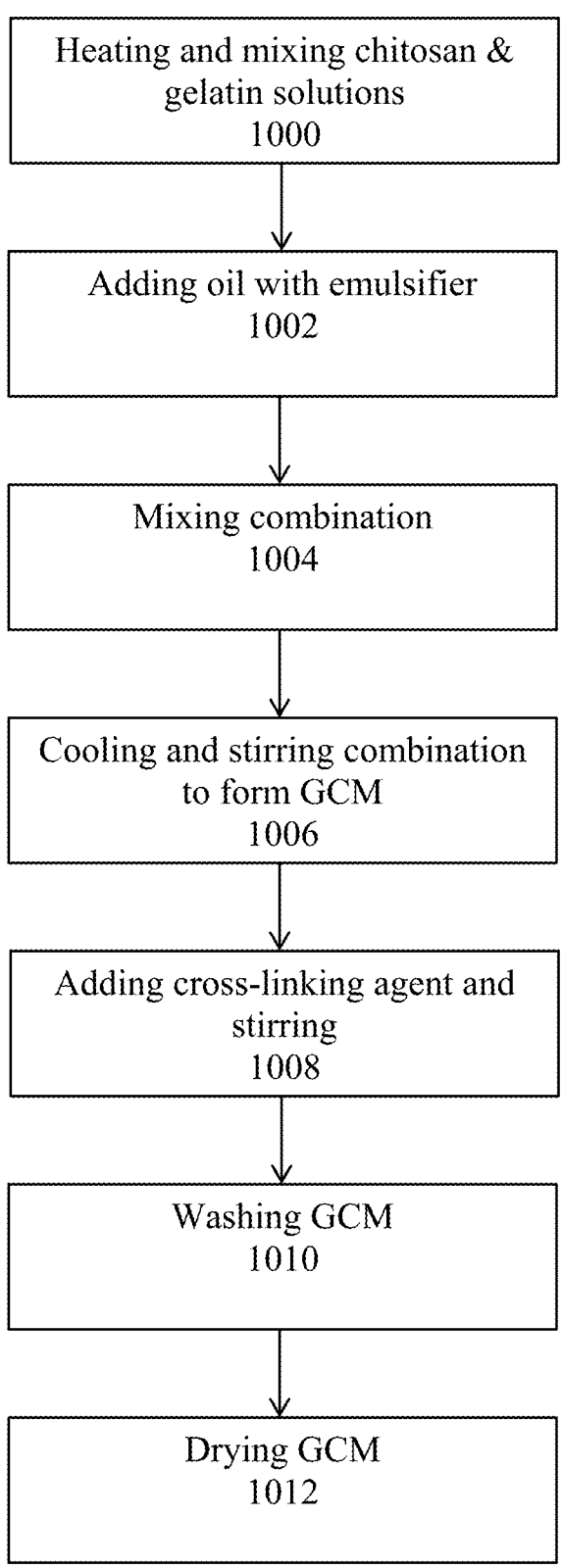
FIG. 10 illustrates a GCM manufacturing method, according to an embodiment of the invention.

FIG. 10 illustrates a GCM manufacturing method, according to an embodiment of the invention. The GCM may be prepared by emulsification techniques, but may also be prepared by spray drying techniques. In the emulsification technique, the chitosan may be dissolved in water containing some acetic acid and mixed with gelatin dissolved in heated water 1000. This mixture may be emulsified with stirring in an organic medium such as olive oil containing an emulsifier with a low hydrophilic-lipophilic balance value, such as polysorbates 1002, 1004. The microspheres may be solidified by decreasing the temperature of the emulsion to below 5 degrees C. with stirring 1006. To make the microspheres insoluble in water, a cross-linking agent may be added to the emulsion 1008. The microspheres may then be washed 1010 to remove the organic medium and any unreacted cross-linking reagents, and harvested using well-known techniques, such as adding organic solvents, e.g. acetone or ether to the emulsion, centrifuging, washing and drying by air or freeze-drying (lyophilizing) 1012.

One or more hemostatic agents may be added to the chitosan/gelatin mixture before emulsification or adsorbed onto the surface of the dried microspheres by freeze-drying or spray-drying a suspension of the microspheres with the hemostatic agent. Alternatively, the dried microspheres may be mixed with a solution containing the hemostatic agent and then subsequently dried for incorporation. The hemostatic agents may include tranexamic acid, adenosine diphosphate, fibrin, fibrinogen, thrombin, calcium, or any agent with hemostatic activity.

In one embodiment of the invention, one or more bioactive agents may be incorporated into the GCM, selected from the group consisting of but not limited to: antimicrobial agents, antibiotics, hormones, proteins, iodine, and colloidal silver.

In one embodiment of the invention, the cross-linking agent is glutaraldehyde. The cross-linker serves to make intermolecular covalent bridges between the polymer chains, and as such, can also include genipin, glyoxal, dextran sulfate, 1,1,3,3-tetramethoxypropane, oxidized cyclodextrins, ethylene glycoldiglyceryl ether, ethylene glycol diglycidyl ether, diiosocyanate, and tripolyphosphate (TPP), among others.

Approximate diameters of the microspheres in some embodiments of the present invention are 5-50 microns, but microspheres with even more rapid hemostatic effects may have diameters in the nanometer range (i.e., 10-999 nanometers) or greater micron range (i.e., 50-999 microns). Preparation of embodiments of the invention in the nanoparticle range to produce nanospheres is similar to that used to produce microspheres, except with faster stirring (e.g., 10,000-20,000 rpm) during the emulsification process and after the cross-linking process (e.g., 5,000-10,000 rpm), and with centrifugation (e.g., at approximately 5,000 rpm for 30 minutes) after the cross-linking process to separate the particles.

EXAMPLE

Equal volumes of chitosan solution containing dilute acetic acid (e.g. 4 weight % chitosan solution in 2% acetic acid solution) and gelatin solution (e.g. 10 weight % in $dH_2O$) were heated to about 80° C. and mixed well. The mixture was then added dropwise to 25x volume of organic oil (e.g. olive oil) containing Tween 80 (e.g. 0.1%), heated to 37° C. and stirred on a stirrer-hotplate. The suspension was mixed (for e.g. 10 minutes), then cooled to 20° C. and stirred for 30 minutes. Glutaraldehyde aqueous solution (e.g. 70%) was added (e.g. at a ratio of 1:2.5 v:v of the original gelatin-chitosan mixture, and stirred for 60 min. The resulting GCM were washed with dilute Tween 80 solution (e.g. 0.1%) 3-6 times to remove the oil. The GCM were then washed with acetone 3-5 times, and then washed with isopropyl alcohol 3-5 times. The GCM were then lyophilized overnight or air dried at 4° C. for at least 7 days (FIG. 1). To determine the approximate size range of the particles, a sample was imaged using an Olympus confocal microscope; this image showed the microparticles range from approximately 5 to 50 micrometers (μm) (FIG. 2).

The dried GCM was tested in an in vitro blood clotting assay against gauze (G) and CombatGauze (CG). Briefly, this assay uses a rotary mixer to continuously mix samples with 1 mL of sheep plasma (SP), which is visually observed for clotting and the time to clot measured in minutes and seconds. In order to facilitate clotting, 2.5-12 μL of 5 M calcium chloride ($CaCl_2$)) in 0.85% saline is added to the SP immediately before the assay begins. Samples were tested in triplicate, and the average results displayed as the average time to clot in seconds. Standard deviations of the averaged values were calculated, and the Student's t-test used to calculate any significant differences between sample groups.

Figure 7:
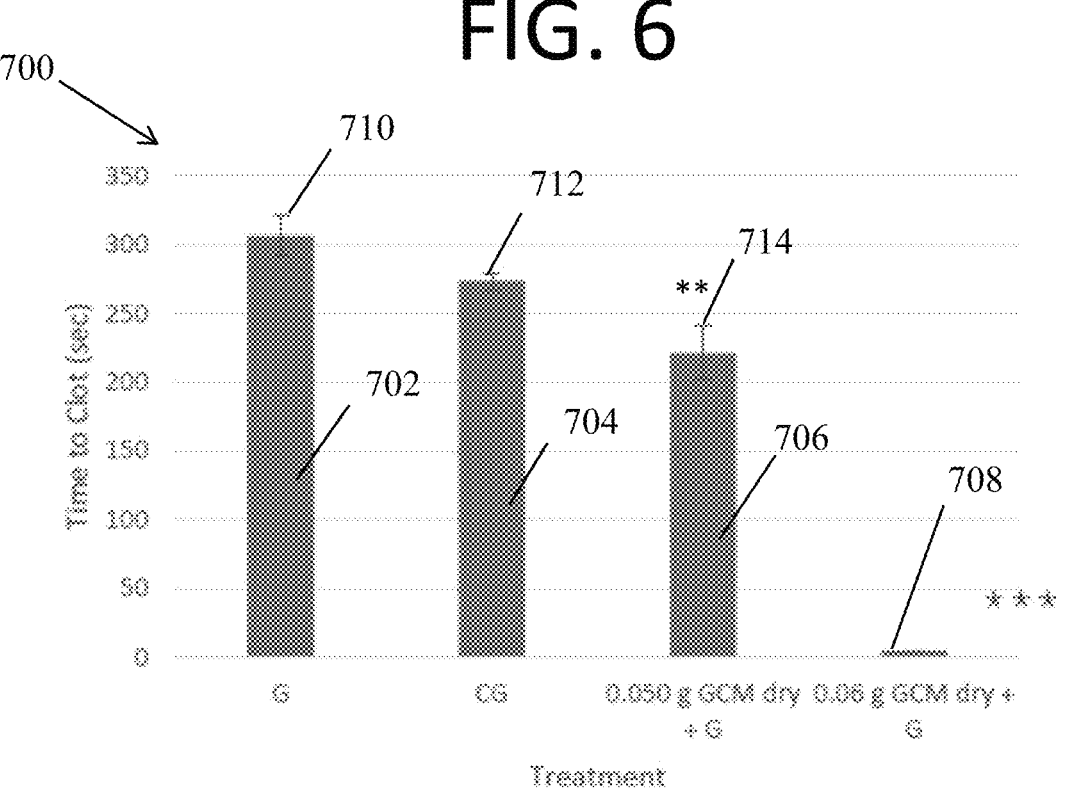
FIG. 7 illustrates results of testing GCM in a hemostasis rotisserie screening assay. G: Gauze. CG: CombatGauze. GCM: gelatin-chitosan microspheres. n=3. , p<0.01. *, p<0.001.

Results 700 are shown in FIG. 7. Results compare performance in time to clot of gauze 702, CombatGauze 704, 0.050 g GCM dry with gauze 706, and 0.06 g GCM dry with gauze 708. The performance of 0.050 g GCM dry with gauze was significantly improved with p<0.01 and the performance of 0.60 g GCM dry with gauze was significantly improved with p<0.001. Error bars 710, 712, 714 apply to the results, respectively. The error bar for 0.06 g GCM dry with gauze is too small to be visible in this chart.

The G sample 702 clotted the SP in 306±14 sec, while CG 704 clotted the SP in 274±6 sec. The GCM at 0.050 gm 706 clotted the SP in 221±20 sec (p<0.01), but at 0.060 g 708 it clotted the SP in 2±0 sec (p<0.001).

Figure 6:
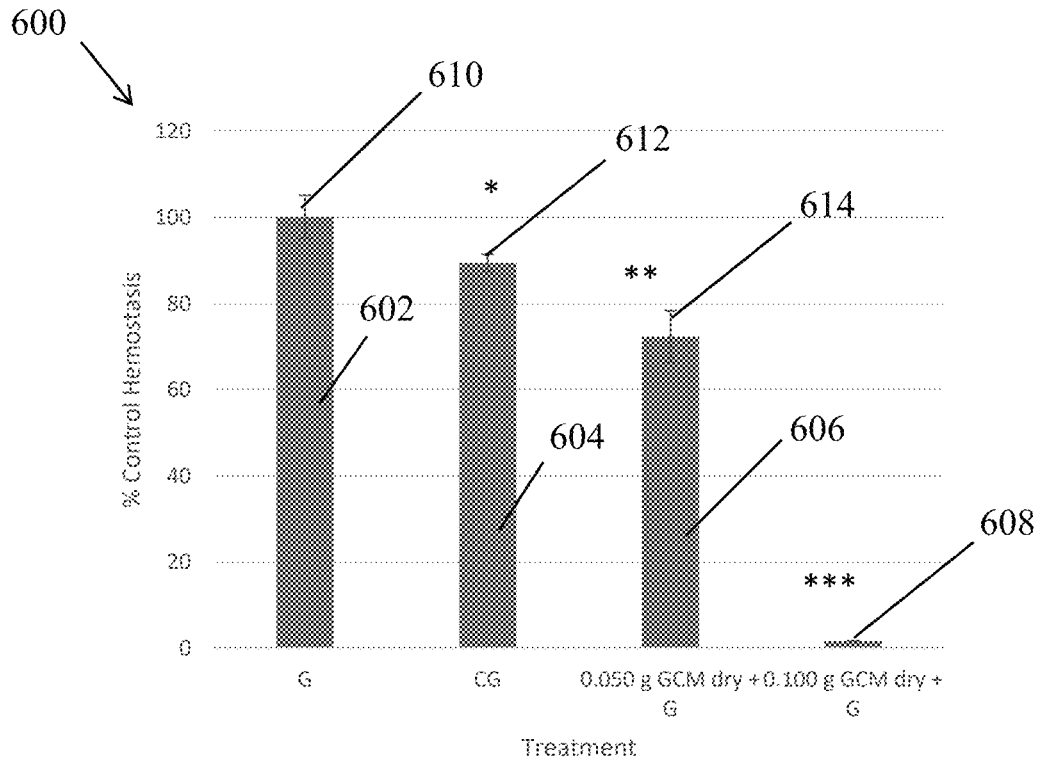
FIG. 6 illustrates results of testing of GCM in a hemostasis rotisserie screening assay. G: Gauze. CG: CombatGauze. GCM at 0.050 (n=3) or 0.100 g (n=2) dry with gauze. *, p<0.05. , p<0.01. *, p<0.001.

FIG. 6 illustrates results 600 of testing of GCM in a similar hemostasis rotisserie screening assay, results expressed as % control hemostasis. Results compare performance in % control hemostasis of gauze 602 (the control), CombatGauze 604, 0.050 g GCM dry with gauze 606, and 0.100 g GCM dry with gauze 608. The performance of CombatGauze was significantly better than gauze with p<0.05, the performance of 0.050 g GCM dry with gauze was significantly improved with p<0.01, and the performance of 0.100 g GCM dry with gauze was significantly improved with p<0.001. Error bars 610, 612, 614 apply to the results, respectively. The error bar for 0.100 g GCM dry with gauze is too small to be visible in this chart.

Further experiments were continued to determine the optimal Tranexamic acid (TXA) and adenosine diphosphate (ADP) concentrations to use for maximum hemostasis rates in the same assay. The following amounts of TXA and ADP solutions have been shown to be most effective: 10 μL of 15 mg TXA/10 mL dH2O (86%±1% of Control); and 1 μL of 0.05 mM ADP (87%±5% of Control). Addition of these compounds to GCM may synergistically work with this material.

Figures 4A, 4B:
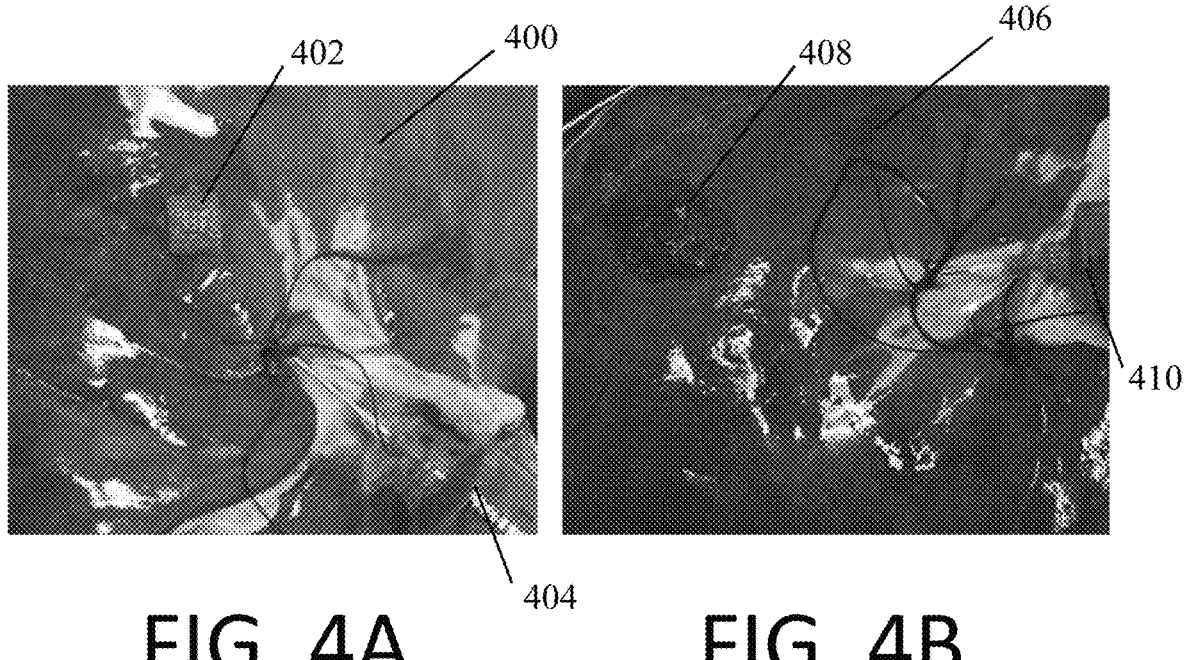
FIGS. 4A-B illustrate CombatGauze (left) and DERT (right) in ex vivo hemostasis experiments in artificially perfused porcine livers, in accordance with one or more implementations.

Prior to testing the GCM in vivo, it was tested ex vivo in a porcine liver artificially perfused with sheep citrated blood. FIG. 4A illustrates CombatGauze and FIG. 4B illustrates DERT in the ex vivo hemostasis experiments in artificially perfused porcine livers 400, 406. Immediately prior to the experiment, 5 M $CaCl_2$) in saline was added to the blood to enable it to clot. The blood was pushed through the tissues through a syringe 404, 410 using a syringe pump at 5 mL per min. An incision was made several inches below the syringe to simulate a liver wound. To provide a pressure-relief route a second similar-sized incision was made approximately 1 cm above this incision. Once the blood began flowing through the simulated wound, the treatment (G, CG, GCM or WS-CG 402 and GCM 408 shown) was applied and the time to clot measured.

Results are summarized in Table 1 below. In this experiment, the simulated wound gauze clotted in about 5:40 minutes. The simulated wound treated with CG clotted in about 2:28 min, the simulated wound treated with WS clotted in about 3:58 min, and the simulated wound treated with 0.203 g of GCM granules clotted in 1:06 min (Table 1). Based on these results, GCM was prepared for testing in vivo.

TABLE 1

Results of ex vivo testing in an artificially perfused porcine liver of GCM vs Gauze, CombatGauze, and WoundSeal.

| Treatment | Clot Time (minutes:seconds) | Amount |
|---|---|---|
| Gauze (G) | 5:40 | 0.20 g |
| Combat Gauze (CG) | 2:28 (n = 2) | 0.200 g |

9

TABLE 1-continued

Results of ex vivo testing in an artificially perfused porcine liver of GCM vs Gauze, CombatGauze, and WoundSeal.

| Treatment | Clot Time (minutes:seconds) | Amount |
|---|---|---|
| GCM | 1:06 (n = 2) | 0.203 g |
| WoundSeal (WS) | 3:58 | 0.200 g |

In vivo testing was completed for Gauze (G), Combat-Gauze (CG) and DERT samples in a rat model of lethal liver injury. Briefly, the median lobe of the liver was excised in anesthetized rats. Five seconds after the hepatectomy, the treatment (0.80 gm of either gauze, CombatGauze, or the DERT formulation contained in a non-reactive mesh pouch) was applied to the cut surface of the liver. Manual pressure was applied for 10 seconds to ensure proper placement of the treatment. The pressure was then released. Evidence of bleeding from the surface of the liver was noted at 5 minutes post-hepatectomy. At this time, any blood in the peritoneal cavity was carefully removed without disturbing the treatment using pre-weighed gauze sponges.

After 30 minutes, shed blood in the abdominal cavity was removed with pre-weighed gauze sponges. The treatment was then removed from the cut liver surface. Total blood loss was calculated as the difference between blood-soaked gauze sponges and treatments minus the weight of the pre-weighed sponges and treatments for each animal. Blood loss was corrected for body weight by expressing the total blood loss as a percentage of total body mass pre-surgery. All measures were presented as mean±standard deviation. Differences in group means were determined with analysis of variance. For measures with differences between group means, direct comparisons of the DERT treatment group with the G and CG groups were performed using the Fisher least significant difference measure. Probabilities <0.05 were considered statistically significant.

Figure 8:
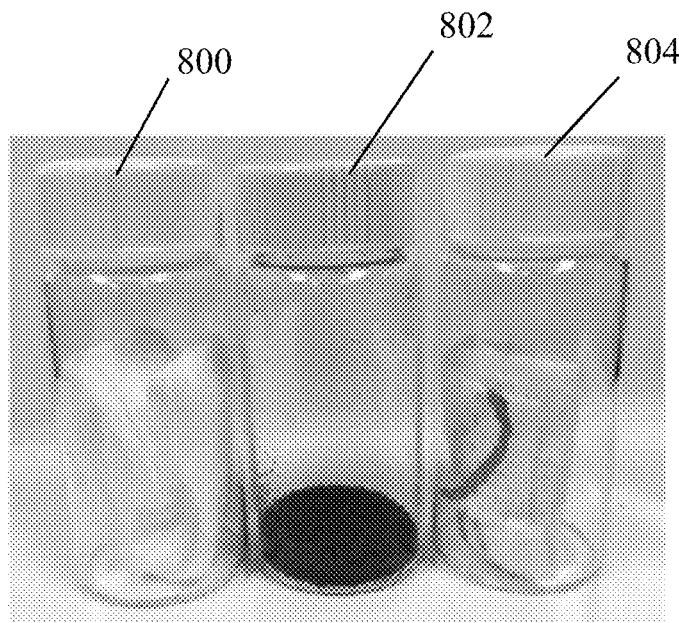
FIG. 8 shows actual amounts of Gauze, GCM and CombatGauze used in the in vivo experiments (0.80 gm each).

Actual amounts of each treatment tested (0.80 gm) are shown in FIG. 8—Gauze 800, GCM 802 and CombatGauze 804.

Figure 9:
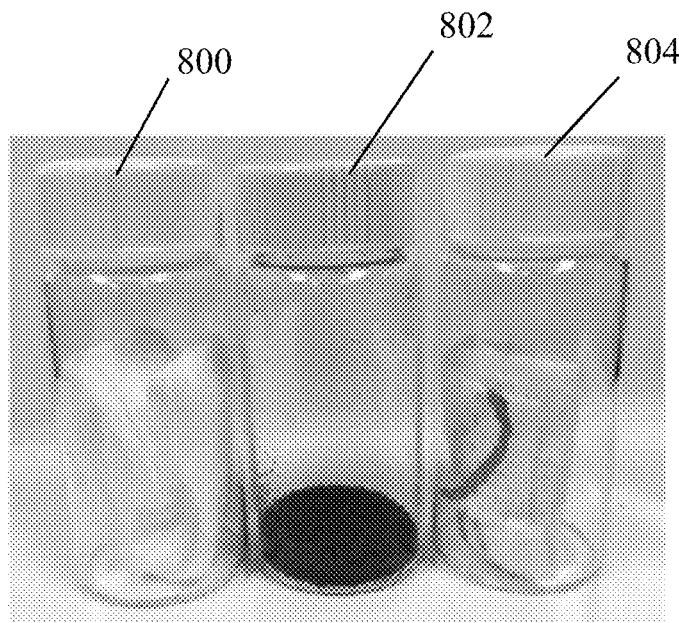
FIG. 9 illustrates results of in vivo testing of Gauze, CombatGauze, and DERT in a rat model of lethal liver injury. n=14, 10, and 15, respectively. *, P<0.001. , P<0.01.

FIG. 9 illustrates results 900 of the in vivo testing of Gauze 902, CombatGauze 904, and DERT 906 in a rat model of lethal liver injury, in terms of blood loss as a percentage of initial body mass. The test had n=14, 10, and 15, respectively, for the three treatments. Error bars 908, 910, 912 apply to the results, respectively. The difference between gauze and CombatGauze and DERT is significant to P<0.01, while the difference between DERT and Com-batGauze was significant with P<0.001.

The results showed that animals treated with Gauze 902 had an average blood loss of 2.14%+0.41% total body mass (n=14); with CombatGauze 904, blood loss of 2.36%+0.52% total body mass (n=10); and with DERT 906, blood loss of 1.44%+0.21% total body mass (n=15). ANOVA analysis of the data followed by F-tests yielded a P-value of 0.000011, suggesting significant differences between the means of the treatment groups. Further analysis of the means between treatment groups using the Fisher least significant difference measure, however, showed highly significant difference between the DERT and G groups (p<0.0015), and significant difference between DERT vs CG (0.010).

Figure 11:
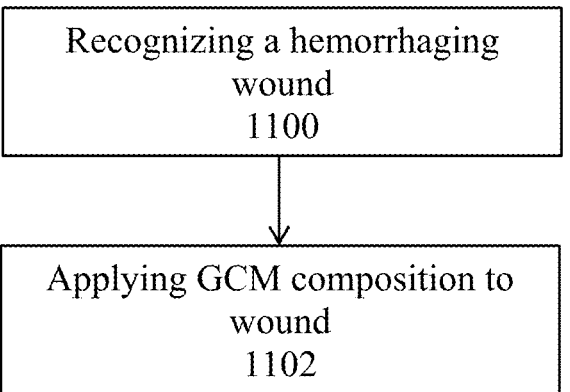
FIG. 11 illustrates a GCM treatment method, according to an embodiment of the invention.

FIG. 11 illustrates a GCM treatment method, according to an embodiment of the invention. A hemorrhaging wound is recognized 1100 and a GCM composition according to an embodiment of the present invention is applied to the wound 1102.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

What is claimed is:

1. A method for manufacturing chitosan-combination microspheres, the method comprising:

heating and mixing equal volumes of a chitosan solution and a gelatin solution, thereby generating an admixture, wherein the heating occurs at a temperature between 40° C. and 80° C.;

adding the admixture to oil containing an emulsifier/surfactant to form a mixture;

stirring the mixture;

adding a 70% glutaraldehyde aqueous solution to the mixture at a volume/volume ratio of 1:2.5 of the admixture, thereby generating chitosan-combination microspheres;

stirring the chitosan-combination microspheres;

washing the chitosan-combination microspheres; and drying the chitosan-combination microspheres, wherein the chitosan-combination microspheres have a diameter of between 50 μm to 999 μm, wherein the washing further comprises:

removing the oil from the chitosan-combination microspheres with a dilute polysorbate 80 solution;

after the removing the oil, washing with acetone; and after the washing with acetone, washing with isopropyl alcohol.

2. The method of claim 1, wherein the emulsifier/surfactant is 0.1% polysorbate 80.

3. The method of claim 1, wherein the drying comprises air drying at 4° C. for at least seven days.

\* \* \* \* \*